United States Patent [19]

Pletcher

[11] Patent Number: 5,322,435
[45] Date of Patent: Jun. 21, 1994

[54] ORTHODONTIC BRACKET

[76] Inventor: Erwin C. Pletcher, 3945 Via Valle Verde, Rancho Sante Fe, Calif. 92067

[21] Appl. No.: 58,524

[22] Filed: May 6, 1993

Related U.S. Application Data

[63] Continuation-in-part of Ser. No. 919,064.

[51] Int. Cl.$^5$ .............................................. A61C 3/00
[52] U.S. Cl. ......................................... 433/11; 433/8; 433/10
[58] Field of Search ................... 433/8, 9, 10, 13, 14, 433/16, 11

[56] References Cited

U.S. PATENT DOCUMENTS

| | | |
|---|---|---|
| 2,549,528 | 4/1951 | Russell .................................. 433/13 |
| 2,627,112 | 2/1953 | Russell . |
| 2,671,964 | 3/1954 | Russell et al. . |
| 3,438,132 | 4/1969 | Rubin . |
| 3,772,787 | 11/1973 | Hanson . |
| 3,780,437 | 12/1973 | Wildman ............................... 433/14 |
| 3,946,488 | 3/1976 | Miller et al. . |
| 4,077,126 | 3/1978 | Pletcher . |
| 4,209,906 | 7/1980 | Fujita . |
| 4,212,638 | 7/1980 | Korn ....................................... 433/8 |
| 4,371,337 | 2/1983 | Pletcher . |
| 4,419,078 | 12/1983 | Pletcher . |
| 4,559,012 | 12/1985 | Pletcher . |
| 4,859,179 | 8/1989 | Kesling .................................. 433/8 |
| 4,917,602 | 4/1990 | Broussard ............................. 433/8 |
| 5,094,614 | 3/1992 | Wildman .......................... 433/10 X |

Primary Examiner—Gene Mancene
Assistant Examiner—Nicholas D. Lucchesi
Attorney, Agent, or Firm—Christie, Parker & Hale

[57] ABSTRACT

A self-locking orthodontic bracket having a body with an archwire slot, and a locking slide member which is movable to open and close the slot. Archwire retention is provided by the slide member without use of conventional ligatures or tie wires. A resilient member is provided to retain the slide member in either the open or closed position, while preventing excessive sliding movement which could disengage the slide member from the bracket body.

9 Claims, 6 Drawing Sheets

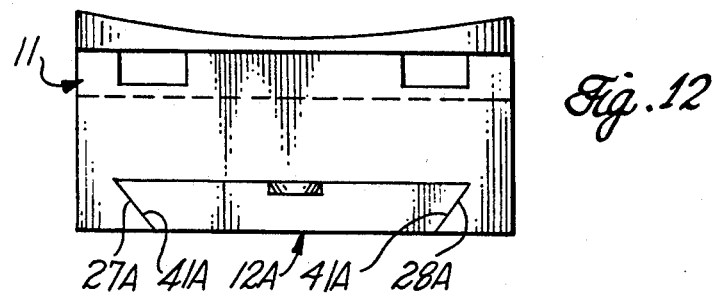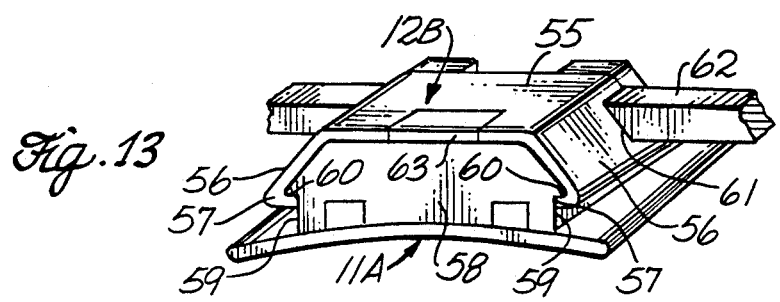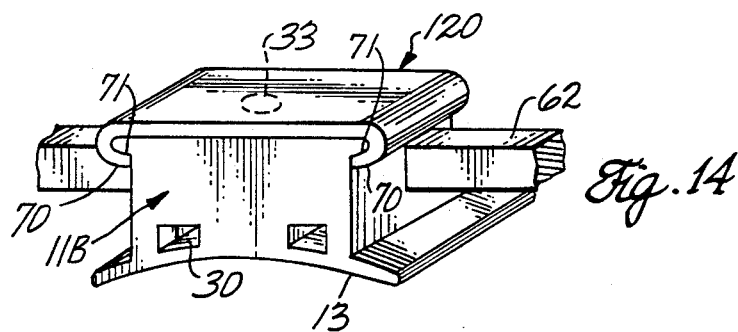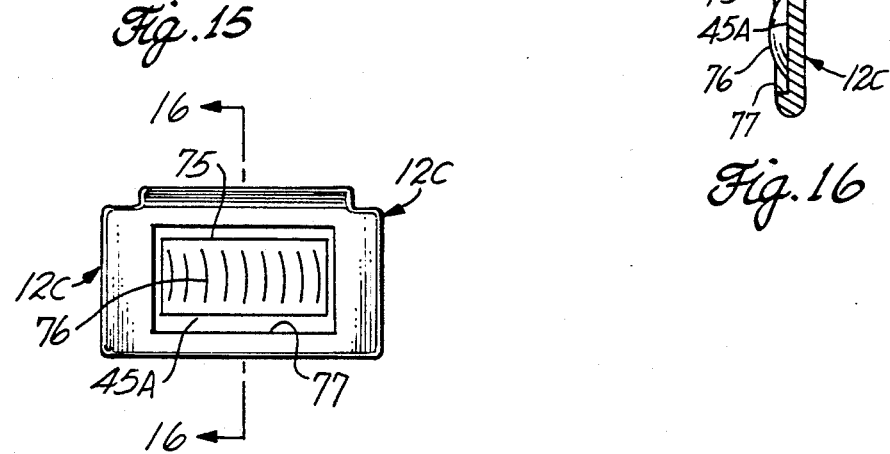

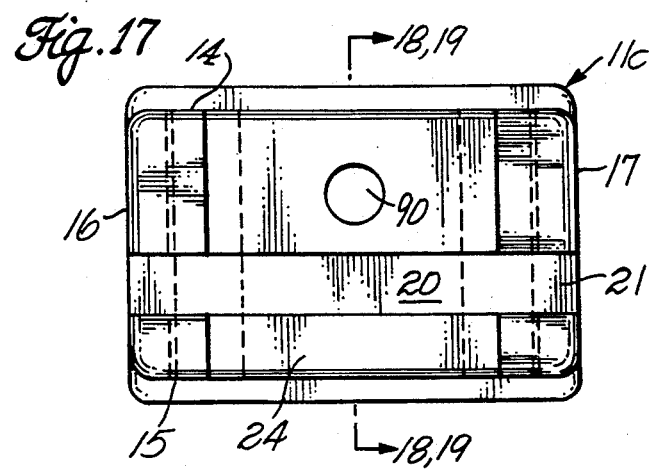
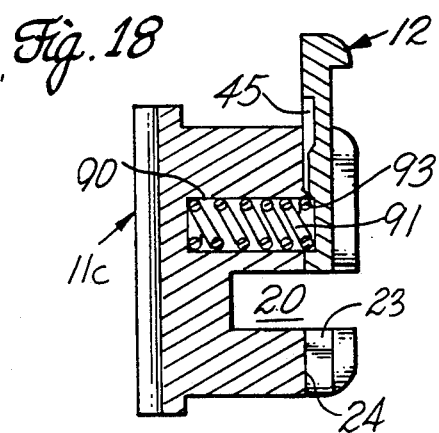
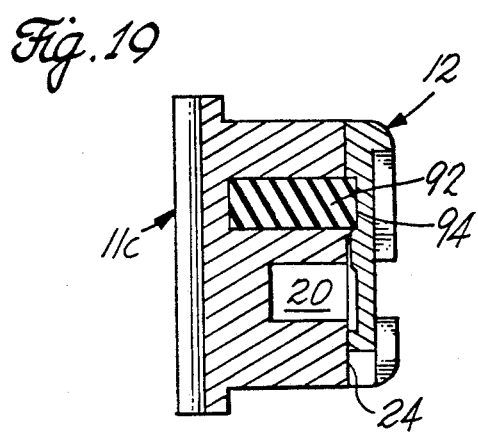

ORTHODONTIC BRACKET

CROSS REFERENCE TO RELATED APPLICATION

This application is a continuation in part of U.S. Pat. application No. 07/919,064 filed Jul. 23, 1992 now pending.

BACKGROUND OF THE INVENTION

Orthodontic treatment of improperly positioned teeth involves the application of mechanical forces to urge the teeth into correct alignment. The most common form of treatment involves use of orthodontic brackets which are small slotted bodies configured for direct cemented attachment to the labial or lingual surfaces of the teeth, or alternatively for attachment to metal bands which are in turn cemented or otherwise secured around the teeth.

A resilient curved archwire is then seated in the bracket slots, and the archwire is bent or twisted before installation whereby the restoring force exerted by the seated resilient wire tends to shift the teeth into orthodontically correct alignment. Depending on the shape of the archwire (both round and rectangular cross sections are in common use) and the orientation of the bracket slot, it is possible to apply forces which will shift, rotate or tip the teeth in any desired direction.

Conventional orthodontic brackets include tie wings around which small ligature wires are tied to hold the archwire in a securely seated position in the brackets. Ligatures or some other form of fastening means are essential to insure that the activated archwire is properly positioned around the dental arch, and to prevent the wire from being dislodged from the bracket slots during chewing of food, brushing of the teeth, or application of other forces to the wire by the patient.

Orthodontists are skilled in the manipulation of ligatures, but the placement of these small wires nevertheless requires considerable time during initial installation of an archwire. It is also normally necessary to remove and replace the ligatures at one or more intermediate stages of orthodontic treatment involving sequential use of several different kinds of archwires, leading to further essentially unproductive chair time for the orthodontist and possible discomfort for the patient.

Ligatures also tend to make proper oral hygiene more difficult as the wires can trap food particles, and the twisted ends of a ligature may be shifted during chewing into a position where irritation of the patient's gums or cheek tissue occurs. Broken or dislodged ligatures may also require emergency patient visits to the orthodontist, and broken ligatures further present the hazard that a loose piece of wire may be swallowed or inhaled into the patient's breathing passages.

Many of the problems presented by ligatures are overcome by self-locking orthodontic brackets which in many cases eliminate need for these tie wires. One approach to a self-locking design involves use of a rotatable locking member which is coupled to the bracket, and is movable to open and close the bracket slot, the archwire being held captive in the slot when the locking member is in the closed position. Bracket configurations of this type are disclosed in my U.S. Pat. Nos. 4,077,126, 4,371,337, 4,419,078 and 4,559,012.

The present invention is directed to a different style of self-locking bracket using a sliding member which is linearly movable in an occlusogingival direction to open and close the bracket archwire slot. This new design has a desirably low profile when mounted on a tooth, and features a detent retention in both the open and closed positions, and with greatly increased resistance to complete removal of the slide member from the bracket body.

The new bracket eliminates any need for time-consuming archwire ligation in a high percentage of cases, and lock-pin sockets are provided to enable ligation in an occasional situation where the archwire cannot be initially seated due to a badly malpositioned tooth. The bracket is smoothly contoured to minimize food-trapping recesses, and is useful in both light-wire and edgewise techniques without restriction on archwire cross section. The bracket is also useful in straight-archwire techniques where desired force vectors (e.g., torque, tip and rotation) are designed into the bracket.

SUMMARY OF THE INVENTION

This invention relates to a two-piece orthodontic-bracket assembly having a bracket body with an archwire slot, and a slide member which is slidably engaged with the body to be movable between a first position in which the archwire slot is open, and a second position in which the slot is closed to retain therein an archwire. A resilient means is provided on and is cooperative between the body and slide member to provide resistance to unintentional movement of the member out of either the open or closed positions. The resilient means is preferably a compressed coil spring or elastomeric plug seated in a socket of the bracket body, and having an end urged against a recessed channel on the inner surface of the slide member. A centrally positioned raised ridge may be formed on the recessed channel to provide further resistance to inadvertent movement of the slide member.

DETAILED DESCRIPTION OF THE DRAWINGS

FIG. 12 is a top view, partly in section, of a modified bracket according to the invention;

FIG. 13 is a pictorial view showing the upper and front surfaces of another modified bracket;

FIG. 14 is a pictorial view showing the upper and front surfaces of yet another modified bracket;

FIG. 15 is a rear elevation of an alternative slide member using a leaf spring;

FIG. 16 is a side sectional elevation on line 16—16 of FIG. 15;

FIG. 17 is a front elevation similar to FIG. 3, and showing a further modified bracket body;

FIG. 18 is a sectional view on line 18—18 of FIG. 17 showing the assembled bracket body and slide member, with a spring resisting slide-member movement; and FIG. 19 is a sectional view similar to FIG. 18, and showing a compressed elastomeric plug to resist slide-member movement.

DETAILED DESCRIPTION OF THE PREFERRED EMBODIMENTS

Figure 1:
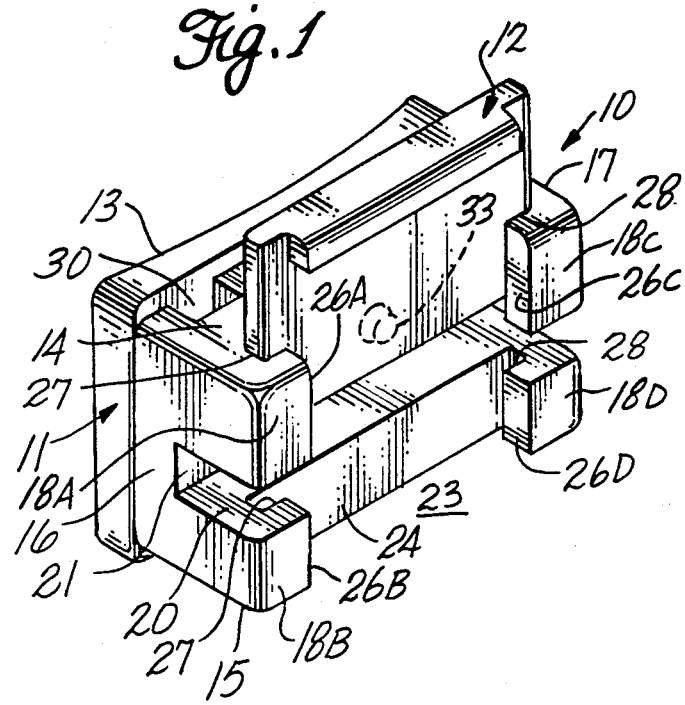
FIG. 1 is a perspective view of an orthodontic bracket according to the invention, and with an archwire-retaining slide member in an open position.
Figure 2:
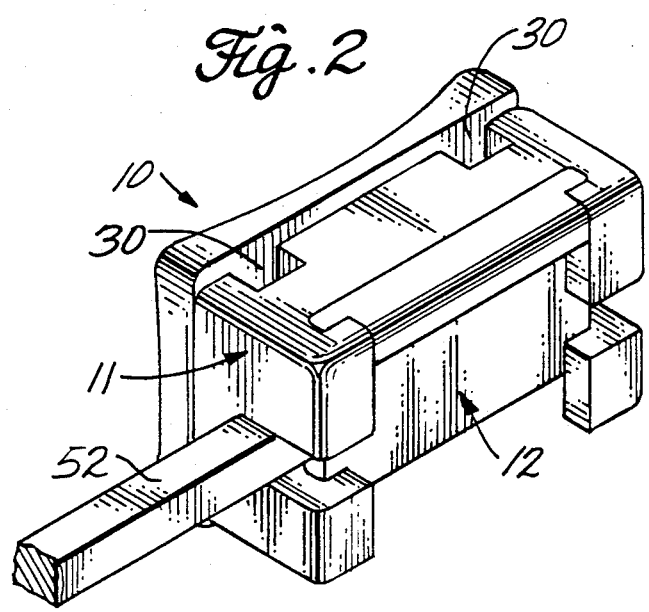
FIG. 2 is a view similar to FIG. 1, but with an archwire fitted in the bracket, and the slide member in a closed position.

A self-locking orthodontic bracket 10 according to the invention is shown in open and closed positions in FIGS. 1 and 2, respectively. The bracket will be described in terms of conventional labial placement (i.e., mounted on the front tooth surface, and facing the lips or cheek tissue), but it is to be understood that the bracket can also be designed for lingual placement on the rear tongue-facing tooth surface.

Figure 3:
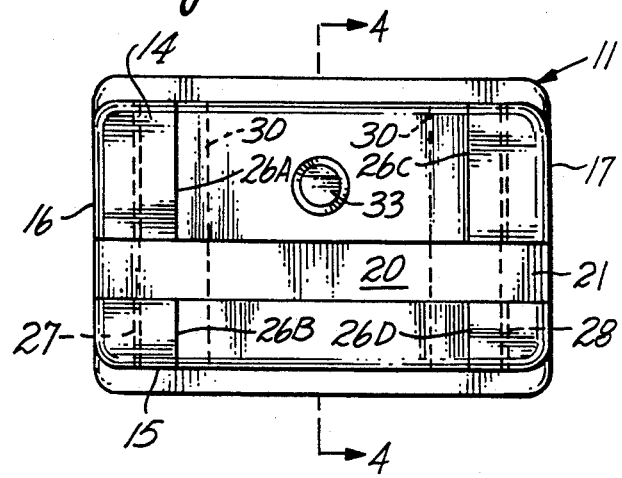
FIG. 3 is a front elevation of a bracket body.
Figure 4:
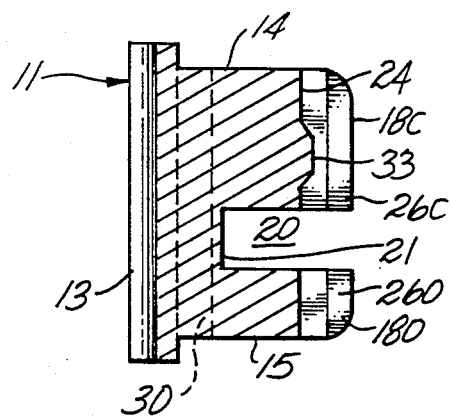
FIG. 4 is a sectional slide elevation on line 4—4 of FIG. 3.
Figure 5:
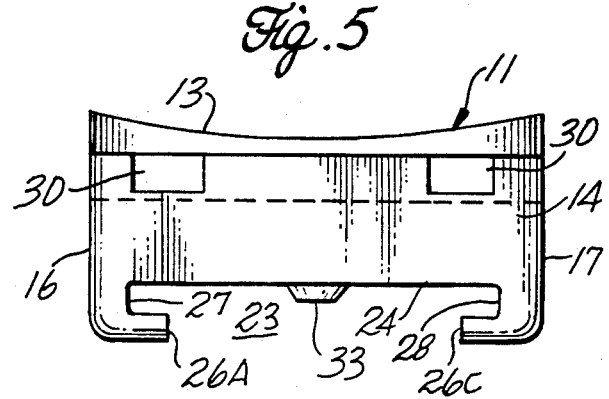
FIG. 5 is a top view of the body, the top and bottom views of the body being symmetrical.

Bracket 10 is a two-piece assembly of a bracket body 11, and a linearly movable locking member or slide member 12 engaged with the bracket body. Bracket body 11, further shown in FIGS. 3-5, is a generally rectangular-in-platform block with a tooth-facing rear surface or base 13 which is concavely contoured for direct cemented attachment to a tooth.

As illustrated, the bracket is configured for use on a lower tooth of the mandibular arch, and has an upper (incisal facing) surface 14, a lower (gingival facing) surface 15, and side (mesiodistally facing) surfaces 16 and 17 at opposite ends of the body. These surfaces extend to front (buccolabial facing) surfaces 18A, B, C and D, the front surfaces being general coplanar. The forward edges and corners of the body block are preferably gently rounded to avoid tissue irritation.

A rectangular and forwardly open archwire slot 20 is formed mesiodistally through the bracket body, and extends part way toward rear surface 12 to a slot base surface 21. The slot is dimensioned to accept rectangular-cross-section archwires of conventional edgewise type, but will also accommodate circular-cross-section or other archwires often used in light-wire preliminary treatment stages.

A slide-member recess 23 is formed in the central forward part of the bracket body, and extends vertically or occlusogingivally through the body from upper surface 14 to lower surface 15. Recess 23 is forwardly open, and extends toward rear surface 12 to a flat floor 24. Archwire slot 20 is substantially deeper than recess 23 so an archwire can be fitted in slot 20 in the space between floor 24 and slot base surface 21 as described below.

Slot 20 and recess 23 separate the front or outer surface of the bracket body into four lugs or projections which terminate in front surfaces 18A-D. The projections have inwardly facing occlusogingivally extending side surfaces 26A-D which are spaced apart by the slot and recess. Depressions are forward in these side surfaces to define a first pair of linearly aligned grooves 27 in side surfaces 26A and B, and a second pair of linearly aligned grooves 28 in side surfaces 26C and D.

A pair of mesiodistally spaced-apart pin slots 30 are formed occlusogingivally through the bracket body between base 13 and slot base surface 21, and spaced slightly inwardly from side surfaces 16 and 17. The pin slots are preferably rectangular in cross section, and are provided to accommodate the shanks of conventional auxiliary anchorage or lock pins (not shown), or to receive a ligature wire in early treatment stages when it may not yet be possible to seat an archwire in slot 20.

A raised detent projection or button 33 is centrally positioned on recess floor 24 between the upper edge of archwire slot 20 and upper surface 14 of the bracket body. The button is preferably formed as a truncated hemisphere or cone, and preferably extends buccolabially forward from the recess floor about 0.006 inch.

The bracket body is preferably an integrally formed component which may be machined, but is also suitable for casting. The body may be made of any of the conventional ceramic, composite, plastic or stainless-steel orthodontic materials which are strong and compatible with in-mouth use.

Figure 6:
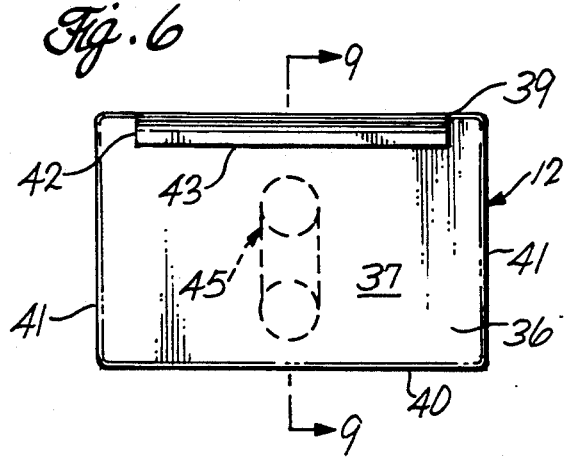
FIG. 6 is a front elevation of the slide member.
Figure 7:
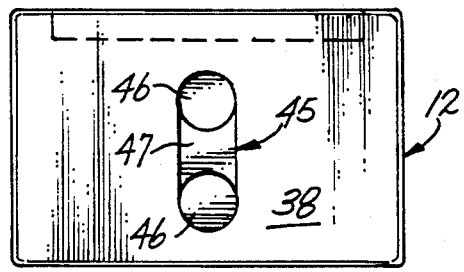
FIG. 7 is a rear elevation of the slide member.
Figure 8:
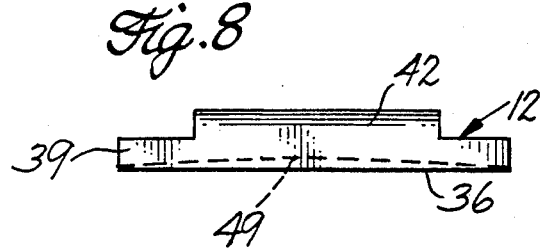
FIG. 8 is a top view of the slide member.

Referring to FIGS. 6-9, slide member 12 has a thin and resilient plate-like body panel 36 with front and rear surfaces 37 and 38, an upper end 39, a beveled lower end 40 (FIG. 9), and opposed side edges 41. The top of the slide member is bent at a right angle to form a forwardly extending bar-like projection 42 at the upper part of panel 36. The projection has an undersurface lip 43 which provides a gripping point when the slide member is to be moved. Projection 42 does not necessarily extend fully across the width of the panel, and preferably terminates short of side edges 41 as shown in FIG. 6.

Figure 9:
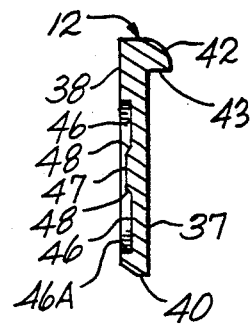
FIG. 9 is a sectional slide view on line 9—9 of FIG. 6.

An elongated detent-button channel 45 is formed in the center of rear surface 38 of the slide-member body panel, and extends parallel to the side edges 41 between a pair of spaced-apart circular seats 46. The seats are separated by a raised ridge 47 in the channel, and the ridge has beveled ends 48 (FIG. 9). In a typical design, slide member 12 is about 0.008 to 0.010-inch thick, and seats 46 have a depth (beneath the plane of rear surface 38) of about 0.006 inch. The shallower central part of channel 45 formed by ridge 47 has a depth of about 0.003 inch.

The width of the slide member between side edges 41 is selected to be only slightly less than the lateral or mesiodistal spacing of bracket-body grooves 27 and 28. The member is made of a slightly flexible or resilient material such as thin stainless steel or plastic. It is important that the member be capable of bowing slightly (as suggested by dashed line 49 in FIG. 8) about the axis of movement when installed in the bracket body.

Assembly of bracket 10 involves only factory installation of the slide member in the bracket body. The lower end of the slide member is inserted into the body, with side edges 41 making a snug slip fit in grooves 27 and 28. The central part of the member is then flexed forwardly (this can be done most easily with a factory installation jig) to enable beveled lower end 40 to pass over button 33 as the member is advanced into the body to position the button in channel 45.

The slide member is now captive in the bracket body, but can be moved between open and closed positions. The open position is shown in FIG. 1, and the lower end of the slide member is positioned slightly above the forwardly open archwire slot in readiness to receive an archwire 52 (FIG. 2). When the archwire is seated, the slide member is lowered to the closed position shown in FIG. 2, and in which the archwire is now captive in the archwire slot. In this closed position, projection 42 makes a slip fit between projection slide surfaces 26A and 26C to provide a smooth contour for the forward occlusal surface of the bracket.

Figure 10:
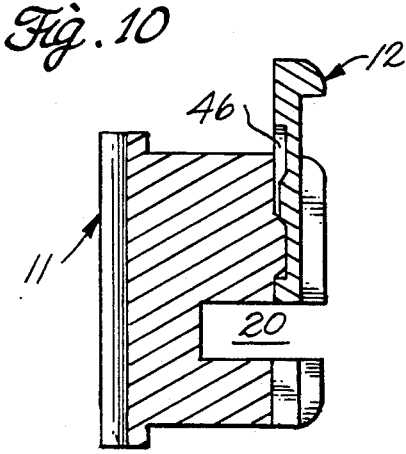
FIG. 10 is a sectional side elevation of the assembled bracket body and slide member, and with the slide member in an open position.
Figure 11:
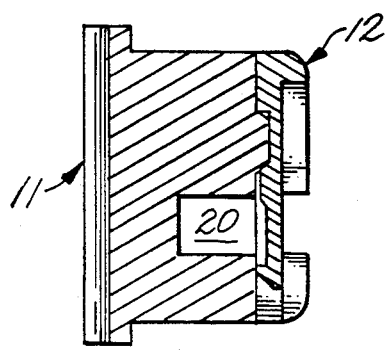
FIG. 11 is a view similar to FIG. 10, but with the slide member in a closed position.

The cooperative relationship of button 43 and channel 45 provides a two-position detent means for retaining the slide member in either the open or closed position. In the open position as best seen in FIG. 10, button 33 is seated in lower channel seat 46 to hold the slide member in that position. Inadvertent uncoupling of the slide member from the bracket body is prevented by the abutting engagement of the lower surface of the button against a deep and blunt lower wall 46A of seat 46.

After the archwire is seated in slot 20, the slide member is moved to the closed position by applying force to projection 42 by either finger pressure, or by a small probe. This closure force causes lower beveled surface 48 of channel ridge 47 to ride over the curved or tapered button surface, and ridge 47 slides over the button crest until the button snaps into the upper seat 46 to secure the slide member in the closed position. The positioning of the button and channel can be reversed (i.e., with the channel on the bracket body, and the button on the slide member), but the above-described configuration is presently preferred for manufacturing convenience.

Reopening of the archwire slot involves only application of force to lip 43 with a probe to shift the slide member back to the open position. The opening and closure forces required to shift the position of the slide member are substantial to avoid unwanted movement by the patient, or during chewing of food. Any risk of such unwanted movement is further minimized by the occlusal positioning of projection 42 such that normal chewing forces urge the slide member toward the closed position.

Although the bracket has been described in terms of a preferred occlusally opening slide member, a reverse arrangement is also feasible in which the member moves gingivally toward the open position. If this reverse configuration is used, the space between the occlusal ends of projection slide surfaces 26A and C is preferably closed by a mesiodistally extending bar (integrally formed with the bracket body) to prevent application of chewing forces which might urge the slide member toward the open position.

Pin slots 30 are provided in the preferred bracket to receive conventional T-head lock pins if auxiliary anchorage is needed for temporary ligatures, intraoral elastics or springs, or interarch appliances sometimes needed in some treatment stages. If desired, however, the slots may be eliminated to achieve an even lower labiolingual profile for the bracket.

The bracket preferably has a mesiodistal width to occlusogingival height ratio of about 1.5 to 1, and the bracket provides excellent control over tooth rotation and other corrective movements. Mesiodistal width is typically about the same as a conventional twin edgewise bracket, but the occlusogingival height is comparatively smaller to enable more gingival bracket placement with resulting increased bite clearance. The bracket base thickness and archwire slot configuration can of course be adjusted for use in either straight-archwire techniques, or in the more traditional bent-archwire procedure.

The bracket has been described in presently preferred form, but a number of variant configurations are feasible, and are within the scope of the invention. For example, and as shown in FIG. 12, a dovetail sliding arrangement may be provided between a modified slide member 12A with beveled or chamfered side edges 41A, and modified mating grooves 27A and 28A in bracket body 11. This arrangement provides a smooth labial or front surface for the bracket assembly.

Another alternative design for arrangement of the slide member and bracket body is shown in FIG. 13 illustrating a modified external wrap-around slide member 12B with a front portion 55, and opposed rearwardly sloping surfaces 56 which terminate in inwardly turned ends 57. A modified bracket body 11A has a correspondingly shaped forward portion 58 defining on each side an inwardly extending recess 59 forming a shoulder 60. Slide-member ends 57 are captive behind shoulders 60 to provide the desired sliding engagement of the slide member and bracket body. The lower ends of sloping surfaces 56 have notches or slots 61 to provide clearance for an archwire 62, and the upper end of front portion 55 has a recess 63 to receive a probe (not shown) used to close the slide member over the archwire.

The detent system already disclosed with reference to bracket 10 is equally useful with the alternative versions just described, but other limited-motion two-position detent arrangements are also suitable. A very simple alternative is to form button 33 on the front of a separate cylindrical plug which is force fitted, threaded, or adhesively secured in a mating cylindrical hole in the bracket body.

Another alternative bracket body 11B is shown in FIG. 14 in combination with a modified wrap-around slide member 12C. The slide member has rearwardly and inwardly turned ends 70 which fit in sliding engagement behind shoulders 71 formed at the forward end of the bracket body. Body 11B has a button 33 just as in body 11, and a cooperating detent-button channel (not shown, but corresponding to that shown in FIGS. 6 and 7) is provided in the rear surface of slide member 12C.

Another variation is illustrated in FIG. 15 and 16 showing a modified slide member 12C having a squared-end channel 45A in which is positioned a bowed leaf spring 75 (seen edge on in FIG. 16). A projecting central portion 76 of the leaf spring flexes and rides over button 33 of the bracket body as the slide member is moved between open and closed positions. A lower surface 77 at the bottom of channel 45 receives and abuts button 33 when the slide member is in the open position to prevent inadvertent separation of the slide member from the bracket body.

Yet another variation uses a bracket body 11C (FIGS. 17-19) which is identical to bracket body 11 (FIG. 3) with the exception that solid detent button 33 is eliminated, and a lingually extending cylindrical blind bore is formed into body 11C at the position formerly occupied by button 33 to define a socket 90. A resilient member such as a coil spring 91 (FIG. 18) preferably made of stainless steel, or a cylindrical plug 92 (FIG. 19) formed of a rubber-like plastic elastomer (suitable materials which are compatible with the environment of the mouth are well known), is seated in the socket.

A forwardly facing end 93 of spring 91, or end 94 of plug 92 extends beyond bracket-body floor 24 across slide-member recess 23 before the slide member is inserted. The spring or plug is then compressed into the socket until the forwardly facing end is flush with floor 24 to permit installation of slide member 12.

The sectional view of FIG. 18 shows the slide member as installed and in the open position, with frictional resistance to unwanted movement being provided by compressed spring 91 with its end 93 urged against the floor of channel 45. FIG. 19 is a similar view with the slide member in a closed position, but showing compressed plug 92 in place of spring 91 to provide frictional resistance to unwanted movement of the slide member between the open and closed position.

In the configuration exemplified by bracket body 11C, the slide member may be relatively stiff, because the needed resiliency is provided by spring 91 or plug 92. If desired, ridge 42 of slide-member channel 42 may be eliminated in this configuration to provide a flat floor for the channel, with the spring or plug providing adequate resistance to unwanted movement of the slide member. Spring 91 or plug 92 are equally useful in alternative bracket embodiments such as shown in FIGS. 12–14.

It is to be understood that the directional terminology herein used is for a labial bracket, and specifically a bracket for a tooth of the lower arch, and appropriate adjustment of the description need be made for a bracket intended for lingual placement. The new bracket is useful on both anterior and posterior teeth of the upper and lower arches, and both width-height ratio and other dimensions of the bracket will be determined by the particular position in the mouth in which the bracket is to be placed.

What is claimed is:

1. A self-locking orthodontic bracket assembly, comprising:
   a bracket body having a tooth-facing base, the body extending forwardly from the base to define a mesiodistally extending and forwardly open archwire slot, the bracket body defining a forwardly open and rearwardly blind socket extending toward the base;
   a slide member engaged with the bracket body to be movable between an open position in which the archwire slot is open, and a closed position in which an archwire in the slot is held captive by the member; and
   a resilient means seated in the socket and urged forwardly against the slide member to retain the slide member in the open and closed positions until substantial force is applied to move the member from one position to the other.

2. A self-locking orthodontic bracket assembly, comprising:
   a bracket body having a tooth-facing base, the body extending forwardly from the base to define a mesiodistally extending and forwardly open archwire slot, the bracket body defining a forwardly open socket extending toward the base; the bracket body further defining opposed grooves;
   a slide member with a body panel having side edges slidably engaged with the opposed grooves of the bracket body to be movable between an open position in which the archwire slot is open, and a closed position in which an archwire in the slot is held captive by the member; and
   a resilient means seated in the socket and urged against the slide member to retain the slide member in the open and closed positions until substantial force is applied to move the member from one position to the other.

3. The assembly defined in claim 2 in which a channel is formed on an inner surface of the slide member, the resilient member extending from the bracket body to bear against a floor surface of the channel.

4. The assembly defined in claim 3, wherein the resilient means is a coil spring.

5. The assembly defined in claim 3, wherein the resilient means is a resilient elastomeric plug.

6. The assembly defined in claim 3 in which the slide-member body panel has a forwardly extending projection forming a lip to enable application of an opening force to the member.

7. The assembly defined in claim 3 in which movement of the slide member toward the open position is in an occlusal direction.

8. The assembly defined in claim 3, in which the bracket body defines an occlusogingivally extending slot therethrough adjacent the base and rearwardly of the archwire slot to receive an auxiliary anchorage means.

9. The assembly defined in claim 3, in which the bracket body defines a pair of mesiodistally spaced-apart occlusogingivally extending slots therethrough adjacent the base and rearwardly of the archwire slot to receive means for auxiliary anchorages.

* * * * *